(12) United States Patent
Shiba

(10) Patent No.: US 6,214,590 B1
(45) Date of Patent: Apr. 10, 2001

(54) 2-AMINOTHIAZOLINE-4-CARBOXYLATE RACEMASE AND GENE ENCODING THEREFOR

(75) Inventor: Toshikazu Shiba, 1-10-34, Higashi 3-chome, Kita-28, Higashi-ku, Sapporo-shi, Hokkaido 065-0028 (JP)

(73) Assignees: Toshikazu Shiba, Hokkaido (JP); Toshie Shiba, Nagano (JP)

( * ) Notice: Subject to any disclaimer, the term of this patent is extended or adjusted under 35 U.S.C. 154(b) by 0 days.

(21) Appl. No.: 09/387,284

(22) Filed: Aug. 31, 1999

(30) Foreign Application Priority Data

Sep. 1, 1998 (JP) .................................................. 10-247365
Apr. 5, 1999 (JP) .................................................. 11-097428

(51) Int. Cl.$^7$ ............................... C12P 13/12; C12N 9/90; C07H 21/04
(52) U.S. Cl. ..................... 435/113; 435/233; 435/252.33; 536/23.7; 536/23.2
(58) Field of Search ...................................... 435/183, 113, 435/69.1, 233, 252.34; 536/23.2, 23.7

(56) References Cited

PUBLICATIONS

Ryu et al. The stability of L–ATC hydrolase participating in the L–cysteine production. Biotechnol. Lett. 1995, vol. 17, pp. 275–280.*
Nippon Nogeikagaku Kaishi, Mar. 5, 1998, Japan.*

* cited by examiner

*Primary Examiner*—Nashaat T. Nashed
*Assistant Examiner*—Christian L. Fronda
(74) *Attorney, Agent, or Firm*—Gray Cary Ware & Freidenrich LLP; Lisa A. Haile

(57) ABSTRACT

There is provided a gene for 2-aminothiazoline-4-carboxylate (ATC) racemase, a recombinant DNA comprising the gene or DNA fragment thereof, a transformant or transductant comprising the recombinant DNA, and a process for preparing the 2-aminothiazoline-4-carboxylate racemase using the transformant or transductant. According to the invention, the ATC racemase may be efficiently produced by microorganisms such as *E. coli* and Pseudomonas and L-cysteine and L-cystine may be efficiently synthesized using the enzyme.

8 Claims, 2 Drawing Sheets

SEQUENCE LISTING

<160> NUMBER OF SEQ ID NOS: 2

<210> SEQ ID NO 1
<211> LENGTH: 1140
<212> TYPE: DNA
<213> ORGANISM: Pseudomonas species
<220> FEATURE:
<221> NAME/KEY: CDS
<222> LOCATION: (191)..(934)

<400> SEQUENCE: 1
cgaagcggcc atcggcgcgc tggagcaggc acttttggcg gtgcagcagc cctgacgggc      60

-continued

```
tcagtacgat gaagcaacaa ttcatcgcca ggcgcaatga atccagcgag atacaccatt        120
agttgagcgt ttgtcctggg tctatgatgc ccatcgccag ttcgattgca ggtatcaccg        180
ggagagtgtc atg aaa cat cat cag acg ggc att gac att gat aac gtc          229
           Met Lys His His Gln Thr Gly Ile Asp Ile Asp Asn Val
            1               5                   10 gag cag cac cgc ccg cgt att ggc ttg att gcg ttg gcg tcg gat gtc          277
Glu Gln His Arg Pro Arg Ile Gly Leu Ile Ala Leu Ala Ser Asp Val
 15                  20                  25 ttg gtc gaa cgt gat ttc tgg cgc atg gcg ctg gtg gca gac gtt gat          325
Leu Val Glu Arg Asp Phe Trp Arg Met Ala Leu Val Ala Asp Val Asp
 30              35                  40                  45 atc gtc acc aca aga att gct cag tcc atg ccg ctg acc ccg caa acg          373
Ile Val Thr Thr Arg Ile Ala Gln Ser Met Pro Leu Thr Pro Gln Thr
             50                  55                  60 ctg gcg aaa ctc gag gac ggc ctg ccg gac gcc gta cgt ctg ctg ttg          421
Leu Ala Lys Leu Glu Asp Gly Leu Pro Asp Ala Val Arg Leu Leu Leu
         65                  70                  75 ccc gag gcc gga ctg gat gcg att gtc ttt gcc tgt acc tcc ggc tcc          469
Pro Glu Ala Gly Leu Asp Ala Ile Val Phe Ala Cys Thr Ser Gly Ser
     80                  85                  90 gcg att atc ggg ccg gcg aaa att gcc cgc cat att gca gcg att cgc          517
Ala Ile Ile Gly Pro Ala Lys Ile Ala Arg His Ile Ala Ala Ile Arg
 95                 100                 105 ccc ggt gtg gcg act acc aac ccg gcc acg gca gcg gtc gag gcg cta          565
Pro Gly Val Ala Thr Thr Asn Pro Ala Thr Ala Ala Val Glu Ala Leu
110                 115                 120                 125 agg cac ctg ggc tgc cgc aga atc gca ttc att gcg ccg tac acc gag          613
Arg His Leu Gly Cys Arg Arg Ile Ala Phe Ile Ala Pro Tyr Thr Glu
                130                 135                 140 gat gtc gcg caa atc acc agc ggt gta ttc agc gat gcg ggt ttt agt          661
Asp Val Ala Gln Ile Thr Ser Gly Val Phe Ser Asp Ala Gly Phe Ser
                145                 150                 155 ttt tct gat cgg gta tgt ttt ggt ctg caa agc gat gtc gag atc gcc          709
Phe Ser Asp Arg Val Cys Phe Gly Leu Gln Ser Asp Val Glu Ile Ala
            160                 165                 170 acc cca ggg ttg gag cat tat ctt cgc gcc atc gcc gag atg gat acc          757
Thr Pro Gly Leu Glu His Tyr Leu Arg Ala Ile Ala Glu Met Asp Thr
        175                 180                 185 gcg aca gcg gat gcg att ttt ctg tcc tgc act acc gcg gca aca ctg          805
Ala Thr Ala Asp Ala Ile Phe Leu Ser Cys Thr Thr Ala Ala Thr Leu
190                 195                 200                 205 gac ttg atc gca ccg ctt gag gcg cac acg ggc ctg ccg gtc att acc          853
Asp Leu Ile Ala Pro Leu Glu Ala His Thr Gly Leu Pro Val Ile Thr
                210                 215                 220 tcg aat cag gca gcg ttc tgg cac acg ctg cag ttg atg ggg cgg acc          901
Ser Asn Gln Ala Ala Phe Trp His Thr Leu Gln Leu Met Gly Arg Thr
                225                 230                 235 gcg ccg ttg cca ggc ctg ggt aaa ttg ttg gcc tagcgccagc gcccaagccc        954
Ala Pro Leu Pro Gly Leu Gly Lys Leu Leu Ala
                240                 245 ttgtcagctc acatcgagct gcaaggcatt gcgcagtgtg gtgagcaact ggtggacgat       1014
cacaggtggc tcgctgtgcg ccgtttcgaa gcgtccgtgc accctgggca gttgcggcag       1074
ccgcggatgc tggagtttca gcagatcgtc cgggcagtct tcctcgggaa tggcggcgat       1134
cgccag                                                                  1140

<210> SEQ ID NO 2
<211> LENGTH: 248
```

```
<212> TYPE: PRT
<213> ORGANISM: Pseudomonas species

<400> SEQUENCE: 2

Met Lys His His Gln Thr Gly Ile Asp Ile Asp Asn Val Glu Gln His
 1               5                  10                  15

Arg Pro Arg Ile Gly Leu Ile Ala Leu Ala Ser Asp Val Leu Val Glu
            20                  25                  30

Arg Asp Phe Trp Arg Met Ala Leu Val Ala Asp Val Asp Ile Val Thr
         35                  40                  45

Thr Arg Ile Ala Gln Ser Met Pro Leu Thr Pro Gln Thr Leu Ala Lys
     50                  55                  60

Leu Glu Asp Gly Leu Pro Asp Ala Val Arg Leu Leu Leu Pro Glu Ala
 65                  70                  75                  80

Gly Leu Asp Ala Ile Val Phe Ala Cys Thr Ser Gly Ser Ala Ile Ile
                 85                  90                  95

Gly Pro Ala Lys Ile Ala Arg His Ile Ala Ala Ile Arg Pro Gly Val
                100                 105                 110

Ala Thr Thr Asn Pro Ala Thr Ala Ala Val Glu Ala Leu Arg His Leu
            115                 120                 125

Gly Cys Arg Arg Ile Ala Phe Ile Ala Pro Tyr Thr Glu Asp Val Ala
    130                 135                 140

Gln Ile Thr Ser Gly Val Phe Ser Asp Ala Gly Phe Ser Phe Ser Asp
145                 150                 155                 160

Arg Val Cys Phe Gly Leu Gln Ser Asp Val Glu Ile Ala Thr Pro Gly
                165                 170                 175

Leu Glu His Tyr Leu Arg Ala Ile Ala Glu Met Asp Thr Ala Thr Ala
            180                 185                 190

Asp Ala Ile Phe Leu Ser Cys Thr Thr Ala Ala Thr Leu Asp Leu Ile
            195                 200                 205

Ala Pro Leu Glu Ala His Thr Gly Leu Pro Val Ile Thr Ser Asn Gln
    210                 215                 220

Ala Ala Phe Trp His Thr Leu Gln Leu Met Gly Arg Thr Ala Pro Leu
225                 230                 235                 240

Pro Gly Leu Gly Lys Leu Leu Ala
                245
```

2-AMINOTHIAZOLINE-4-CARBOXYLATE RACEMASE AND GENE ENCODING THEREFOR

BACKGROUND OF THE INVENTION

1. Field of the Invention

The present invention relates to a 2-aminothiazoline-4-carboxylate racemase gene, a recombinant DNA, a transformant or transductant, a 2-aminothiazoline-4-carboxylate racemase enzyme, a process for preparing the enzyme, and a process for preparing L-cysteine or L-cystine using the enzyme.

2. Prior Art

Bacteria belonging to the genus Pseudomonas are known as a representative of microorganisms converting DL-2-aminothiazoline-4-carboxylate, hereinafter abbreviated as DL-ATC, into L-cysteine (Japanese Patent Application Laid-open Publication No. 51-70881), and the cells thereof have hitherto used in the synthesis reactions of L-cysteine (Japanese Patent Publication No. 53-25037). Racemization of DL-ATC is required for efficient conversion of DL-ATC into L-cysteine and enzymatic racemization of DL-ATC is considered to take place in the above mentioned bacteria. However, these conventional bacteria only produce insufficient amounts of racemase and the efficiency of producing L-cysteine from starting DL-ATC is poor. Further, there has been no report on isolation of the above mentioned enzyme or the cloning of its gene.

SUMMARY OF THE INVENTION

It is an object of the present invention to provide a 2-aminothiazoline-4-carboxylate racemase gene, a process for preparing the 2-aminothiazoline-4-carboxylate racemase enzyme by expressing the gene, and a process for preparing L-cysteine or L-cystine using said enzyme.

In order to achieve such an object, the present inventors have made great efforts to enhance amounts of desired enzyme produced by cloning a racemase enzyme gene from bacteria possessing the enzyme and enhancing its genetic amplification, transcription and translation activities. Thus, the present invention has been completed.

Accordingly, the present invention provides a DNA fragment comprising a 2-aminothiazoline-4-carboxylate racemase gene and having the following restriction enzyme cleavage map and 4.8 kilo base pairs (kb):

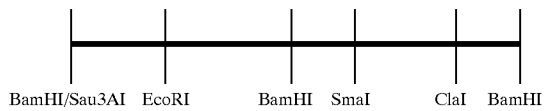

Also, the present invention provides a 2-aminothiazoline-4-carboxylate racemase gene coding for the following protein (a) or (b):

(a) a protein comprising the amino acid sequence as shown in SEQ ID NO:2; or
(b) a protein comprising an amino acid sequence in which one or more amino acids have been deleted from, replaced in or added to the amino acid sequence (a), and having a 2-aminothiazoline-4-carboxylate racemase activity.

An example of the above mentioned gene includes the gene having a base sequence of from 191st to 937th bases of SEQ ID NO:1.

Further, the present invention provides a recombinant DNA comprising the 2-aminothiazoline-4-carboxylate racemase gene or a DNA fragment of the gene in a vector DNA.

Still further, the present invention provides a transformant or transductant comprising the above mentioned recombinant DNA.

According to the present invention, a process for preparing a 2-aminothiazoline-4-carboxylate racemase is also provided which comprises cultivating the above mentioned transformant or transductant in a culture medium and collecting the 2-aminothiazoline-4-carboxylate racemase from the culture medium.

Further provided is a 2-aminothiazoline-4-carboxylate racemase comprising the following protein (a) or (b):

(a) a protein comprising the amino acid sequence as shown in SEQ ID NO:2; or
(b) a protein comprising an amino acid sequence in which one or more amino acids have been deleted from, replaced in or added to the amino acid sequence (a), and having a 2-aminothiazoline-4-carboxylate racemase activity.

According to the present invention, there is further provided a process for preparing L-cysteine or L-cystine comprising contacting a DL-2-aminothiazoline-4-carboxylate with the 2-aminothiazoline-4-carboxylate racemase of claim 2 or 7 to produce L-cysteine or L-cystine.

BRIEF DESCRIPTION OF THE DRAWINGS

Hereinbelow, the present invention will be described in detail with reference to the attached drawings in which.

DESCRIPTION OF THE INVENTION

Figure 1:
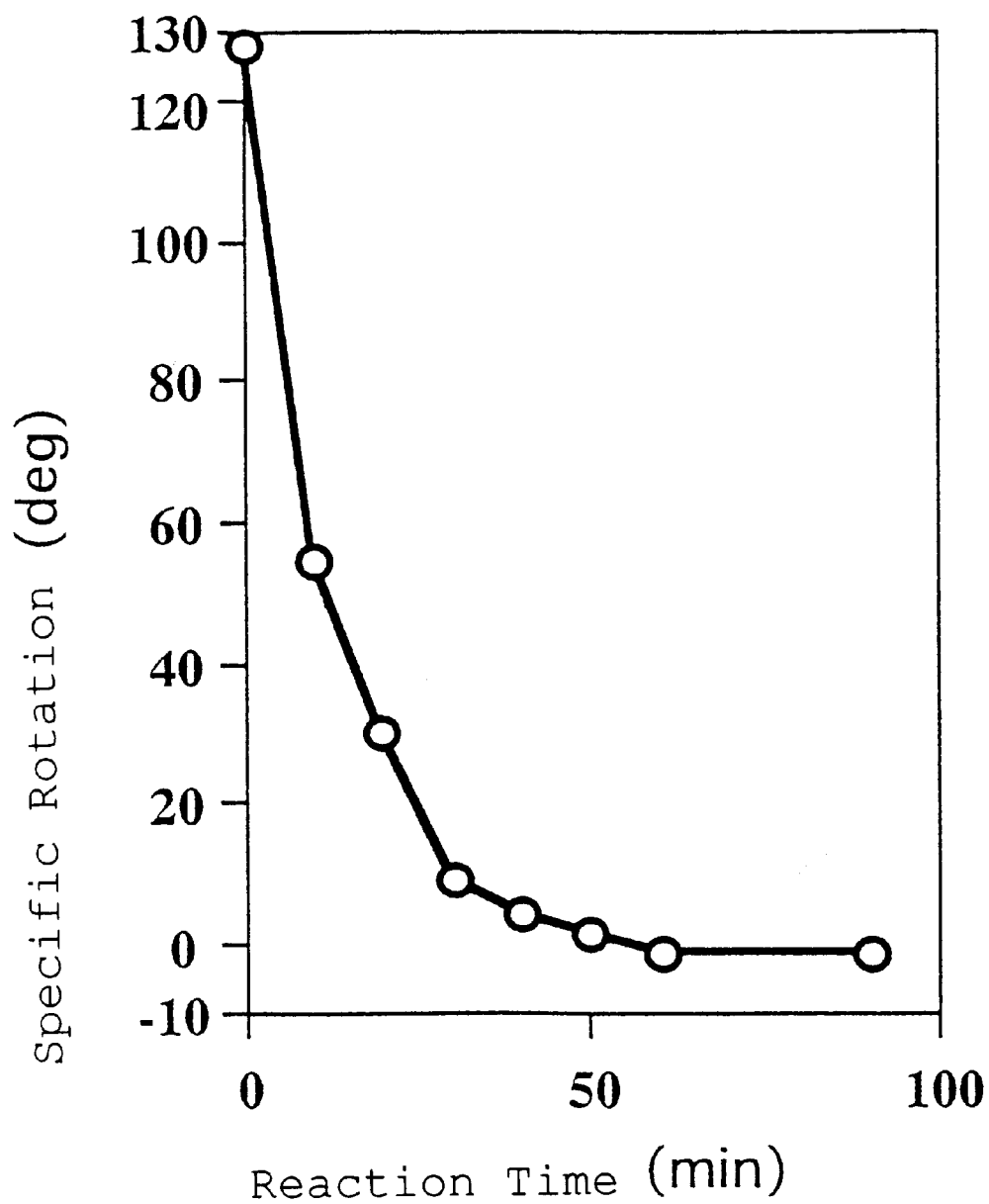
FIG. 1 shows the results of racemization of D-ATC by a crude extract from E. coli in which ATC racemase (ORF1) was highly expressed.

ATC to be racemized according to the present invention is represented by the following formula (I):

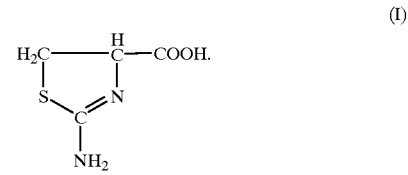

Compounds to be racemized according to the present invention include not only ATC but also ATC derivatives, examples of which include all optical isomers having a thiazoline ring and represented by the formula (II):

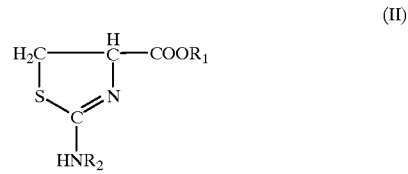

wherein each of R1 and R2 represents a methyl, ethyl, propyl, butyl or the like group.

Donors of a gene coding for ATC racemase according to the present invention may be any microorganisms which produce this enzyme. For example, a bacterium capable of converting DL-ATC into L-cysteine, Pseudomonas ovalis strain BS, is encompassed and the present inventors utilized this bacterium to clone a gene coding for an ATC racemase.

(1) Preparation of Mutant Strain of ATC Racemase Gene

Pseudomonas ovalis strain BS (FERM P-16965) was treated with nitrosoguanidine to induce mutation. The treated bacterium was screened for mutant strains which were capable of growing by utilizing DL-ATC as a sole nitrogen source but incapable of growing by utilizing D-ATC as a sole nitrogen source. A desired mutant strain MM7 was thus isolated and used as a mutant strain of the gene coding for ATC racemase.

(2) Cloning of Gene

A genome DNA was prepared from Pseudomonas ovalis strain BS (FERM P-16965) according to the method of Current Protocols in Molecular Biology, unit 2.4 and partially digested with restriction enzyme Sau3AI. The resulting DNA fragment was ligated into plasmid vector pME294 (Antonie van Leuwenhoek 54:567–573 (1988)) which had been cut with restriction enzyme BamHI and treated with phosphatase. The recombinant DNA was used to transform the mutant strain (MM7) and the resulting transformant was plated in an agar medium containing D-ATC as a sole nitrogen source. Transformants having a recombinant DNA containing the desired gene converts D-ATC into L-ATC, utilizes L-ATC as a nitrogen source, grows in the agar medium to form a colony, and can be isolated easily.

The transformant from the colony formed on the selection medium was cultivated to prepare a plasmid DNA and a plasmid containing an inserted DNA portion of about 4.8 kb in size was obtained and designated as pMM717.

(3) Determination of Base Sequence

The plasmid pMM717 was digested with various restriction enzymes to prepare a restriction enzyme map of the resulting inserted DNA portion. Based on the analysis results, a DNA fragment of about 3.5 kb obtained by digesting pMM717 with restriction enzymes EcoRI and ClaI was subcloned into plasmid vector pBluescriptII (Stratagene). The subcloned insert DNA portion was sequenced by the dideoxy method using various synthetic DNAs as primers to determine the base sequence. The results revealed the presence of an open reading frame (ORF1) having about 23% identity with the gene coding for 5-substituted hydantoin racemase (Japanese Patent Application Laid-open Publication No. 4-271784) in amino acid sequence level.

The thus determined full base sequence and the amino acid sequence of the polypeptide translated from the base sequence are shown in SEQ ID NOs:1 and 2, respectively.

All genes having one or more, preferably one or few, amino acids deleted from, replaced in or added to the amino acid sequence as shown in SEQ ID NO:2 and coding for a 2-aminothiazoline-4-carboxylate racemase providing the 2-aminothiazoline-4-carboxylate racemase enzyme activity, are encompassed in the present invention.

To obtain a gene having one or more, preferably one or few, amino acids deleted from, replaced in or added to the amino acid sequence as shown in SEQ ID NO:2 and coding for a 2-aminothiazoline-4-carboxylate racemase providing the 2-aminothiazoline-4-carboxylate racemase enzyme activity, any method may be used, including, for example, site-specific mutagenesis which is a known technique for producing point or deletion mutation in a gene; a method in which a gene is selectively cleaved and a selected nucleotide is then removed from or added to it to ligate the gene; and the oligonucleotide mutagenesis.

(4) Converting Ability Encoded by Plasmid pMM717

The plasmid pMM717 was digested with restriction enzyme SmaI and the resulting DNA fragment of about 2.6 kb was ligated into an E. coli expression vector pTrc99A (Amersham Pharmacia Biotech) digested with SmaI. The resulting ligated plasmid (pTmm208) was used to transform E. coli JM109 and ampicillin resistance was used as an indication to yield transformants. The plasmid pTmm208 contained ORF1 in the same direction with trc promoter on the vector. The transformants were cultivated, and isopropyl β-D-thio-galactopyranoside (IPTG) was added to the culture medium in order to induce the expression of ORF1. The crude extract of the strain in which the expression of ORF1 was induced contained the activity to convert D-ATC into L-ATC. Further, analysis of the crude extract by SDS-polyacrylamide gel electrophoresis revealed overexpression of a protein with a molecular weight of about 25,000 daltons. These results showed that ORF1 coded for ATC racemase. The molecular weight calculated from the amino acid sequence of ORF1 was 26,379 which was almost identical with the molecular weight of the overexpressed protein as observed in the electrophoresis.

(5) Process for Producing the Enzyme Using ATC Racemase Gene

When a microorganism, such as Escherichia coli JM109 (pTmm208) (FERM P-16966), to which a recombinant DNA comprising the DNA fragment containing the ATC racemase gene of the present invention and a vector DNA has been introduced is cultivated in a suitable medium and D-ATC or L-ATC is added thereto, racemic ATC is obtained. The same results may also be obtained if ATC racemase is prepared from the microorganism and the enzymatic reaction is carried out. Further, the method of the present invention may also be applicable to a synthesis system of L-cysteine or L-cystine, wherein the ATC racemase utilizing DL-ATC as a substrate is used to efficiently convert D-ATC into L-ATC and a group of enzymes converting L-ATC into L-cysteine (or a microorganism containing such a group of enzymes or its extract) is also used to synthesize L-cysteine or L-cystine. For example, the gene is introduced into a microorganism having an ability to synthesize L-cysteine from DL-ATC, to improve the producing ability for L-cysteine.

The above mentioned E. coli may be cultivated in a similar manner as in conventional aerobic culture of general microorganisms. Generally, shaking culture in a liquid medium or aerobic stirring culture is preferred. Media used contain glucose, glycerol, sucrose, galactose, starch etc. as a carbon source, and yeast extract, peptone, meat extract, corn steep liquor etc. as a nitrogen source. Inorganic salts used may include mono- or di-potassium phosphate, magnesium sulfate, sodium or magnesium chloride, ferric chloride, ferric sulfate, manganese sulfate etc. The medium may also contain DL-ATC as a inducer substrate for the present enzyme. The cultivation is carried out at an initial pH of 7 to 9, a temperature of 20 to 42° C. for 4 to 24 hours.

After cultivation, ATC racemase may be collected from the culture by any means used to recover usual enzymes. For example, the cells are disrupted in a conventional ultrasonic treatment or dissolved by a lytic enzyme such as lysozyme to extract the desired enzyme. The resulting crude enzyme is then purified by various chromatographic means such as ion exchange chromatography and gel filtration.

EXAMPLES

Hereinbelow the present invention will be described in more detail by way of examples which do not limit the scope of the present invention in any way.

Example 1

(1) Preparation of Mutant Strain of ATC Racemase Gene

*Pseudomonas ovalis* strain BS was cultivated in 5 ml LB medium [a liquid medium comprising LB Broth Base (GIBCO BRL) in distilled water, pH 7.4] at 30° C. overnight. The cells were collected by centrifugation and suspended in 5 ml of 0.15 M NaCl after discarding the liquid medium and the suspension was further centrifuged. After discarding the supernatant, the cells were suspended in 0.15 M NaCl containing 0.01 mg/ml nitrosoguanidine and allowed to stand at room temperature for 15 minutes. After centrifugation, the supernatant was discarded. The cells were suspended in 5 ml of 0.15 M NaCl and diluted. Then, the cells were plated in LB medium containing 1.5% agar to yield at least 5,000 colonies. The resulting colonies were transferred by replica plating to M9 minimal medium (Current Protocols in Molecular Biology, unit 1.1) containing DL-ATC or D-ATC as a sole nitrogen source. The composition of this medium is shown below.

0.6% Na2HPO$_4$ (subscript)
0.3% KH2PO$_4$ (subscript)
0.05% NaCl
0.2% DL-ATC or D-ATC
1 mM MgSO$_4$(subscript)
0.2% Glucose
1.5% Agar About 3,000 colonies were replicated and a strain which did not grow in a medium containing D-ATC but grew in a medium containing DL-ATC was isolated and designated as MM7. It was considered that MM7 had a mutation in ATC racemase gene and could not grow in M9 minimal medium containing D-ATC as a sole nitrogen source since it could not convert D-ATC into L-ATC.

(2) Preparation of Chromosomal DNA of *Pseudomonas ovalis* Strain BS

Twenty (20) ml of LB culture were placed in a 100 ml Erlenmeyer flask and sterilized at 120° C. for 15 minutes. One platinum loop of stock slant of *Pseudomonas ovalis* strain BS was inoculated and subjected to shaking culture at 30° C. for 20 hours. After culture, the medium was centrifuged at 5,000 rpm for 10 minutes to isolate cells. These cells were treated according to the method described in Current Protocols in Molecular Biology, unit 2.4 to yield chromosomal DNA.

Then, 0.2 mg of the chromosomal DNA and 0.2 unit of restriction enzyme Sau3AI (Takara Shuzo) were mixed in 50 mM Tris-HCl buffer containing 100 mM NaCl and 10 mM MgSO4 (pH 7.4) and allowed to react at 37° C. for 1 hour to effect partial digestion of DNA. After the reaction was completed, the reaction mixture was subjected to 0.7% agarose gel electrophoresis to excise DNA bands corresponding to about 6 kb to 10 kb. The DNA in the gel was extracted using QIAEX II Gel Extraction Kit (manufactured by QIAGEN) and purified to yield 5 μg of chromosomal DNA fragment.

(3) Preparation of Chromosomal DNA Library of *Pseudomonas ovalis* Strain BS Using Plasmid Vector pME294 (Antonie van Leeuwenhoek 54:567–573 (1988)) and Search for DNA Fragments Containing ATC Racemase Gene Two (2) μg of plasmid vector pME294 and 1 unit of restriction enzyme BamHI (Takara Shuzo) were mixed in 50 mM Tris-HCl buffer containing 100 mM NaCl and 10 mM MgSO$_4$ (subscript) (pH 7.4) and allowed to react at 37° C. for 2 hours. The resulting digestion mixture was then subjected to phenol extraction and ethanol precipitation in a conventional manner to yield plasmid vector pME294 digested with BamHI.

Then, 100 ng of DNA fragment of the plasmid vector pME294 digested with BamHI was mixed with 200 ng of the chromosomal DNA fragment partially digested with Sau3AI obtained in (2) above and the DNAs were ligated in a conventional manner using DNA ligation kit (Takara Shuzo). The thus obtained mixture containing the recombinant plasmid DNA was introduced into MM7 by electroporation according to the method in Current Protocols in Molecular Biology, unit 1.8. The transformant was applied on LB medium and subjected to static culture at 37° C. for 24 hours. The resulting colonies were transferred (in replica method) to fresh LB medium and M9 minimal medium containing D-ATC as a sole nitrogen source set forth in (1) above and one colony which grew as well in the M9 minimal medium containing D-ATC as a sole nitrogen source was obtained from about 4,000 colonies.

(4) Analysis of Base Sequence of ATC Racemase Gene and Search for ATC Racemase Gene According to the method described in Current Protocols in Molecular Biology, unit 1.6, plasmids were extracted from the colonies obtained in (3) above and purified to yield plasmid pMM717 having the inserted DNA fragment of 4.8 kb at BamHI site of pME294. The plasmid pMM717 was digested with EcoRI and ClaI to yield about 3.5 kb DNA fragment in the insert. This DNA fragment was subcloned into *E. coli* plasmid vector pBluescript II (Staratagene). The resulting subcloned plasmid was used as a template to determine the base sequence of each DNA fragment. The determination of base sequence was carried out in a conventional manner using various synthetic DNA as primers, BigDye Terminator Cycle Sequencing Ready Reaction Kit (manufactured by Perkin-Elmer Applied Biosystems) and DNA sequencer (manufactured by Perkin-Elmer Applied Biosystems).

The analysis of the total base sequence of 4.8 kb DNA fragment containing ATC racemase gene derived from *Pseudomonas ovalis* strain BS revealed 3 open reading frames. It was confirmed that the primary amino acid sequence of one of the open reading frames, ORF1 consisting of 747 bases coding for 248 amino acids, has about 23% identity with the primary amino acid sequence of 5-substituted hydantoin racemase gene (Japanese Patent Application Laid-open Publication No. 4-271784).

The base sequence of the resulting ATC racemase gene of *Pseudomonas ovalis* strain BS and its vicinities and the primary amino acid sequence of the polypeptide translated from the base sequence are shown in SEQ ID NO:1 and SEQ ID NO:2, respectively. The restriction enzyme map of the 4.8 kb DNA fragment from *Pseudomonas ovalis* strain BS cloned in pMM717 was prepared on the basis of the base sequence and is shown below.

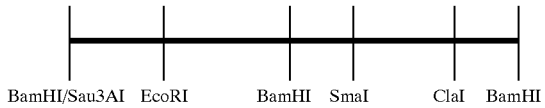

On the restriction enzyme map, ORF1 exists on the about 1.6 kb EcoRI-BamHI fragment in the direction from BamHI to EcoRI.

The plasmid pMM717 was digested with restriction enzyme SmaI (Takara Shuzo). The resulting about 2.6 kb DNA fragment (SmaI site also exists in the vector sequence near BamHI/Sau3AI) was ligated with *E. coli* expression vector pTrc99A (Amersham Pharmacia Biotech) which had also been digested with SmaI. This about 2.6 kb DNA fragment contains only ORF1 and does not contain any other open reading frame. The resulting plasmid pTmm208 was used to transform *E. coli* JM109 and screened for transformants using ampicillin resistance as an indicator. The plasmid pTmm208 has ORF1 inserted in the same direction as trc promoter in the vector pTrc99A and can induce the expression of ORF1 by the addition of isopropyl-β-D-thiogalactopyranoside (IPTG) to the culture medium. The transformed *Escherichia coli* JM109 (pTmm208) (FERM P-16966) was subjected to shaking culture in 5 ml LB culture at 37° C. until the absorbance of the culture at 600 nm reached 0.3 (early logarithmic growth phase). At this time, 1 mM IPTG was added to the culture and shaking culture was further continued for 4 hours. After culture, cells were collected by centrifugation, suspended in 1 ml of 20 mM Tris-HCl buffer (pH 7.5), 2.5mM dithiothreitol, and disrupted by ultrasonic treatment. The disrupted cells were centrifuged and the supernatant was taken as a crude extract containing ATC racemase. A tenth (1/10) volume of this crude extract was added to 20 mM Tris-HCl buffer (pH 7.5), 2.5 mM dithiothreitol containing 0.02% D-ATC. The resulting reaction mixture for determining ATC racemase activity was incubated at 30° C. A sample was taken at a certain time interval, mixed with an equal amount of 5% TCA to stop the reaction, and then centrifuged to precipitate denatured proteins. A specific rotation of the supernatant after the centrifugation was measured as an indicator of ATC racemase activity. The change of the ATC racemase activity with time is shown in FIG. 1. The specific rotation of D-ATC became zero at one hour after the start of the reaction due to progress of the racemization reaction, indicating that about half of D-ATC molecules in the reaction mixture was converted into L-ATC. These results revealed that an activity to convert D-ATC into L-ATC was present in the crude extract of the strain in which the expression of ORF1 was induced. Upon analysis of the crude extract by SDS-polyacrylamide gel electrophoresis, it was observed that a protein having a molecular weight of about 25,000 daltons was overexpressed. Accordingly, it was proved that ORF1 codes for ATC racemase. Further, the molecular weight calculated from the amino acids of ORF1 is 26,379 daltons which was almost same as the molecular weight of the overexpressed protein observed in the electrophoresis.

Example 2
Synthesis of L-cysteine and L-cystine Using Crude Extract Containing ATC Racemase Overexpressed in *E. coli*.

Amounts of L-cysteine and L-cystine synthesized were measured in a mixture of the crude extract from *E. coli* containing ATC racemase prepared in a similar manner with Example 1 and a crude extract from *Pseudomonas ovalis* strain BS capable of converting DL-ATC into L-cysteine (prepared by the method described in Japanese Patent Publication No. 54-2272). A reaction mixture of *E. coli* crude extract containing no racemase with Pseudomonas crude extract was used as a control. The synthesis reaction of L-cysteine and L-cystine was carried out in the following reaction system.

Figure 2:
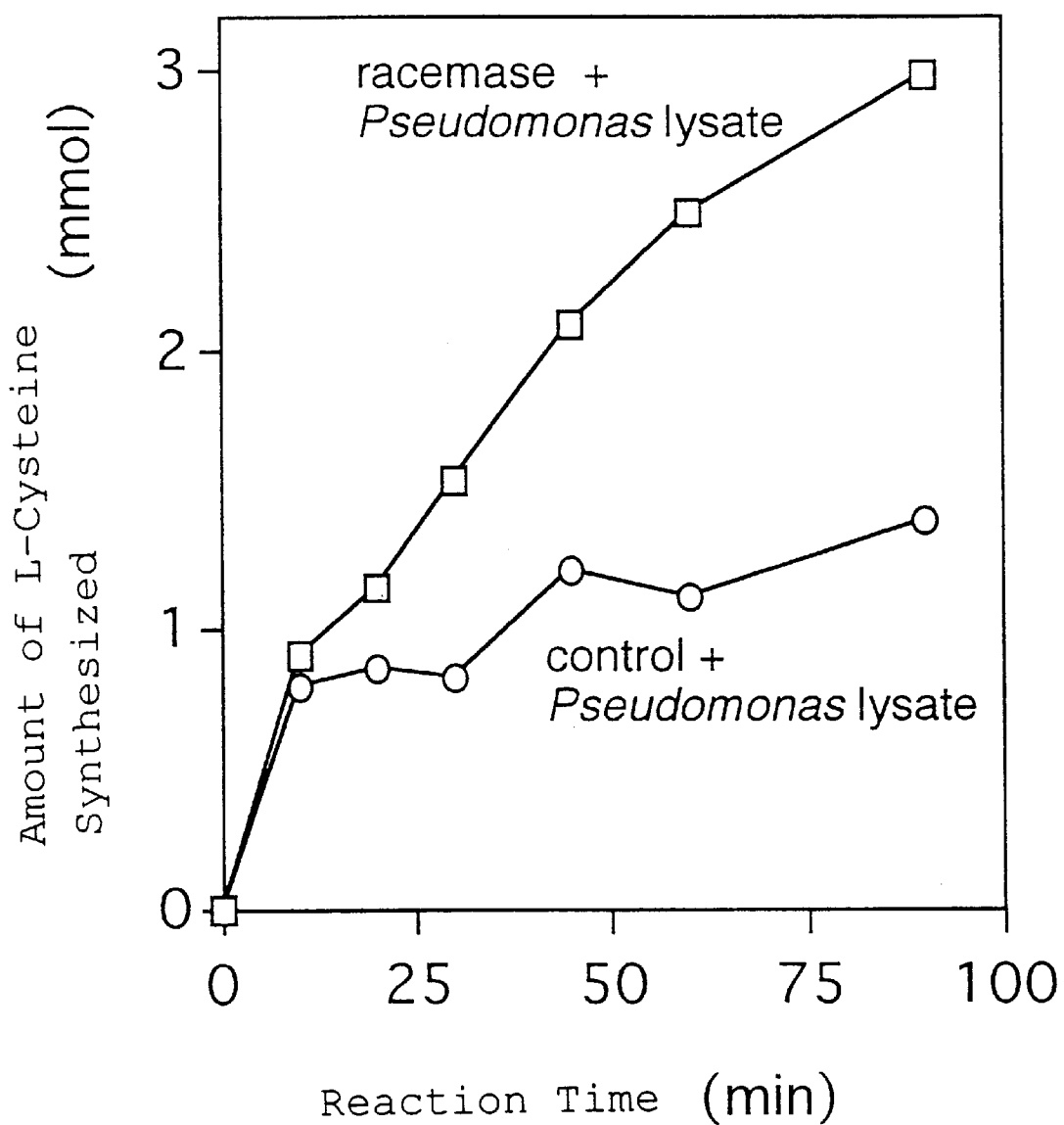
FIG. 2 shows promotion of L-cysteine synthesis efficiency of a Pseudomonas crude extract (lysate) by a crude extract from E. coli in which ATC racemase was highly expressed.

20 mM Tris-HCl (pH 8.0)
5 mM $MgSO_4$ (subscript)
5 mM $MnSO_4$ (subscript)
2.5 mM hydroxylamine
1 mM DTT
1% DL-ATC
176 mg Pseudomonas crude extract
88 mg *E. coli* crude extract The reaction was carried out at 30° C. and a sample was taken from the reaction mixture at a certain time interval. Hydrochloric acid was added at a final concentration of 1 N to stop the reaction while simultaneously solubilizing the insoluble L-cystine. Then, an equal amount of 4% N-ethylmaleimide was added to the reaction mixture and allowed to stand overnight. The synthesized L-cysteine and L-cystine were quantified by the ninhydrin method. The results are shown in FIG. 2. The synthesis reaction of L-cysteine was faster in samples comprising *E. coli* crude extract in which ATC racemase was highly expressed. In FIG. 2, squares represent the amount of L-cysteine synthesized in the mixture of *E. coli* crude extract in which ATC racemase was highly expressed with Pseudomonas crude extract; and circles represent the amount of L-cysteine synthesized in the mixture of *E. coli* crude extract without racemase and Pseudomonas crude extract. The results of FIG. 2 indicate that the ATC racemization reaction may be a rate-limiting step in the synthesis reaction of L-cysteine by Pseudomonas. Therefore, it maybe concluded that the synthesis of L-cysteine can be made more efficient by highly expressing ATC racemase of the present invention.

Advantages of the Invention

The present invention provides a gene for ATC racemase, a recombinant DNA comprising the gene, a transformant or transductant comprising the recombinant DNA, and a process for preparing the ATC racemase. According to the invention, the ATC racemase may be efficiently produced by microorganisms such as *E. coli* and Pseudomonas and L-cysteine and L-cystine may be efficiently synthesized using the enzyme or a microorganism highly expressing the enzyme.

What is claimed is:

1. An isolated DNA fragment from *Pseudomonas ovalis* which encodes a 2-aminothiazoline-4-carboxylate racemase, has the following restriction enzyme cleavage map and comprises approximately 4.8 kb base pairs:

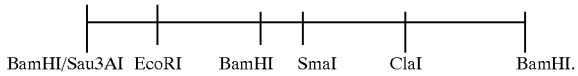

BamHI/Sau3AI   EcoRI   BamHI   SmaI   ClaI   BamHI.

2. An isolated DNA fragment encoding a protein comprising the amino acid sequence as shown in SEQ ID NO:2.

3. The DNA fragment according to claim 2, having from about nucleotide 191 to 937 in SEQ ID NO: 1.

4. A recombinant DNA fragment according to claims 1, 2 or 3 in a vector.

5. A transformant or transductant comprising a recombinant DNA fragment according to claim 4.

6. A process for preparing a 2-aminothiazoline-4-carboxylate racemase comprising cultivating a transformant or transductant accoring to claim 5 in a culture medium and collecting the 2-aminothiazoline-4-carboxylate racemase from the culture.

7. An isolated 2-aminothiazoline-4-carboxylate racemase comprising the amino acid sequence as shown in SEQ ID NO:2.

8. A process for preparing L-cysteine or L-cystine comprising contacting a DL-2-aminothiazoline-4-carboxylate with the 2-aminothiazoline-4-carboxylate racemase according to claim 7 to produce L-cysteine or L-cystine.

* * * * *